(12) United States Patent
Pickus et al.

(10) Patent No.: US 12,002,591 B2
(45) Date of Patent: Jun. 4, 2024

(54) DETECTION OF ANOMALOUS COMPUTING ENVIRONMENT BEHAVIOR USING GLUCOSE

(71) Applicant: DexCom, Inc., San Diego, CA (US)

(72) Inventors: Sarah Kate Pickus, San Diego, CA (US); Brian Bober, San Diego, CA (US)

(73) Assignee: Dexcom, Inc., San Diego, CA (US)

( * ) Notice: Subject to any disclaimer, the term of this patent is extended or adjusted under 35 U.S.C. 154(b) by 261 days.

(21) Appl. No.: 17/455,277

(22) Filed: Nov. 17, 2021

(65) Prior Publication Data
US 2022/0165432 A1    May 26, 2022

Related U.S. Application Data

(60) Provisional application No. 63/117,705, filed on Nov. 24, 2020.

(51) Int. Cl.
*G16H 50/70* (2018.01)
*A61B 5/00* (2006.01)
*A61B 5/145* (2006.01)
*G16H 10/60* (2018.01)
(Continued)

(52) U.S. Cl.
CPC ......... *G16H 50/70* (2018.01); *A61B 5/14532* (2013.01); *A61B 5/6801* (2013.01); *A61B 5/7278* (2013.01); *A61B 5/742* (2013.01); *A61B 5/746* (2013.01); *G16H 10/60* (2018.01); *G16H 40/67* (2018.01); *G16H 50/20* (2018.01)

(58) Field of Classification Search
CPC ........ G16H 50/70; G16H 10/60; G16H 40/67; G16H 50/20; G16H 40/63; A61B 5/14532; A61B 5/6801; A61B 5/7278; A61B 5/742; A61B 5/746; A61B 5/7275
USPC .......................................................... 705/2–3
See application file for complete search history.

(56) References Cited

U.S. PATENT DOCUMENTS

| | | | |
|---|---|---|---|
| 2014/0221966 A1* | 8/2014 | Buckingham | A61M 5/14244 604/504 |
| 2020/0196925 A1* | 6/2020 | Lin | A61B 5/14507 |
| 2020/0245913 A1* | 8/2020 | Dalal | G06N 3/088 |

OTHER PUBLICATIONS

International Search Report and Written Opinion for Application No. PCT/US21/59640, dated Mar. 25, 2022, 20 pages.

* cited by examiner

*Primary Examiner* — Joy Chng
(74) *Attorney, Agent, or Firm* — Patterson + Sheridan, LLP

(57) ABSTRACT

Detection of anomalous computing environment behavior using glucose is described. An anomaly detection system receives glucose measurements and event records during a first time period. Missing events that are missing from the event records during the first time period are identified by processing the glucose measurements using an event engine simulator. An anomaly detection model is generated based on the missing events during the first time period. Subsequently, the anomaly detection system receives additional glucose measurements and additional event records during a second time period. Missing events that are missing from the additional event records during the second time period are identified by processing the additional glucose measurements using the event engine simulator. Anomalous behavior is detected if the identified missing events that are (Continued)

missing from the event records during the second time period are outside a predicted range of missing events of the anomaly detection model.

23 Claims, 8 Drawing Sheets

(51) Int. Cl.
*G16H 40/67* (2018.01)
*G16H 50/20* (2018.01)

DETECTION OF ANOMALOUS COMPUTING ENVIRONMENT BEHAVIOR USING GLUCOSE

This application claims the benefit of U.S. Provisional Patent Application No. 63/117,705, filed Nov. 24, 2020, and titled "Detection of Anomalous Computing Environment Behavior Using Glucose," the entire disclosure of which is hereby incorporated by reference.

BACKGROUND

Diabetes is a metabolic condition affecting hundreds of millions of people, and is one of the leading causes of death worldwide. For people living with Type I diabetes, access to treatment is critical to their survival and it can reduce adverse outcomes among people with Type II diabetes. With proper treatment, serious damage to the heart, blood vessels, eyes, kidneys, and nerves, due to diabetes can be avoided. Regardless of a type of diabetes (e.g., Type I or Type II), managing it successfully involves monitoring and oftentimes adjusting food and activity to control a person's blood glucose, such as to reduce severe fluctuations in and/or generally lower the person's glucose.

Conventional glucose monitoring systems are employed to monitor a user's glucose using glucose monitoring devices, and to output glucose measurements to the user. As part of this, conventional glucose monitoring systems may also generate various events, such as a low glucose alert that can be output when the user's glucose levels are below, or predicted to be below, a low glucose threshold. Users of conventional glucose monitoring systems may come to rely on these events and alerts in order to take mitigating actions to prevent dangerous glucose-related conditions from occurring.

Unfortunately, a variety of different circumstances may cause conventional glucose monitoring systems to fail to generate certain events. Such circumstances can include signal loss between the glucose monitoring device and a computing device of the user, issues with the glucose monitoring device, operating system incompatibility issues, resource competition, user actions, and so forth. As an example, installation of a new operating system or an update to a new version of the operating system for a particular brand of mobile device, may result in an incompatibility issue between the mobile device and the glucose monitoring device which causes the glucose monitoring application to fail to generate certain events.

Conventionally, the only way for an application developer to detect and fix an issue that is causing the glucose monitoring application to miss events is based on user feedback. Users of a glucose monitoring device, for example, may notice that their glucose monitoring application is failing to output low glucose alerts, and thus submit a complaint. When enough complaints are received, an investigation may begin to determine a solution to the issues causing the missing events. However, this conventional process for missing event detection is slow and usually requires a critical number of users to detect the issue before an investigation can be initiated. Moreover, some missing events may not even be noticed by users, and thus will not be detected based on user complaints. The inability to detect missing events early on can lead to harmful, or even life threatening issues for users who rely on the accuracy of events and alerts generated by glucose monitoring applications and devices. Thus, it is important to detect missing events generated by glucose monitoring applications as early as possible.

SUMMARY

To overcome these problems, detection of anomalous computing environment behavior using glucose is leveraged. An anomaly detection system receives glucose measurements collected by wearable glucose monitoring devices and event records associated with the glucose measurements during a first time period. Missing events that are missing from the event records during the first time period are identified by processing the glucose measurements using an event engine simulator. An anomaly detection model is generated based on the missing events during the first time period. The anomaly detection model includes a predicted range of missing events during a second time period that is non-anomalous, where the second time period is subsequent to the first time period. The anomaly detection system also receives additional glucose measurements collected by the wearable glucose monitoring devices and additional event records associated with the additional glucose measurements during the second time period. Missing events that are missing from the additional event records during the second time period are identified by processing the additional glucose measurements using the event engine simulator. Anomalous behavior is detected if the identified missing events that are missing from the event records during the second time period are outside the predicted range of missing events of the anomaly detection model.

This Summary introduces a selection of concepts in a simplified form that are further described below in the Detailed Description. As such, this Summary is not intended to identify essential features of the claimed subject matter, nor is it intended to be used as an aid in determining the scope of the claimed subject matter.

BRIEF DESCRIPTION OF THE DRAWINGS

The detailed description is described with reference to the accompanying figures.

DETAILED DESCRIPTION

Overview

Figure 1:
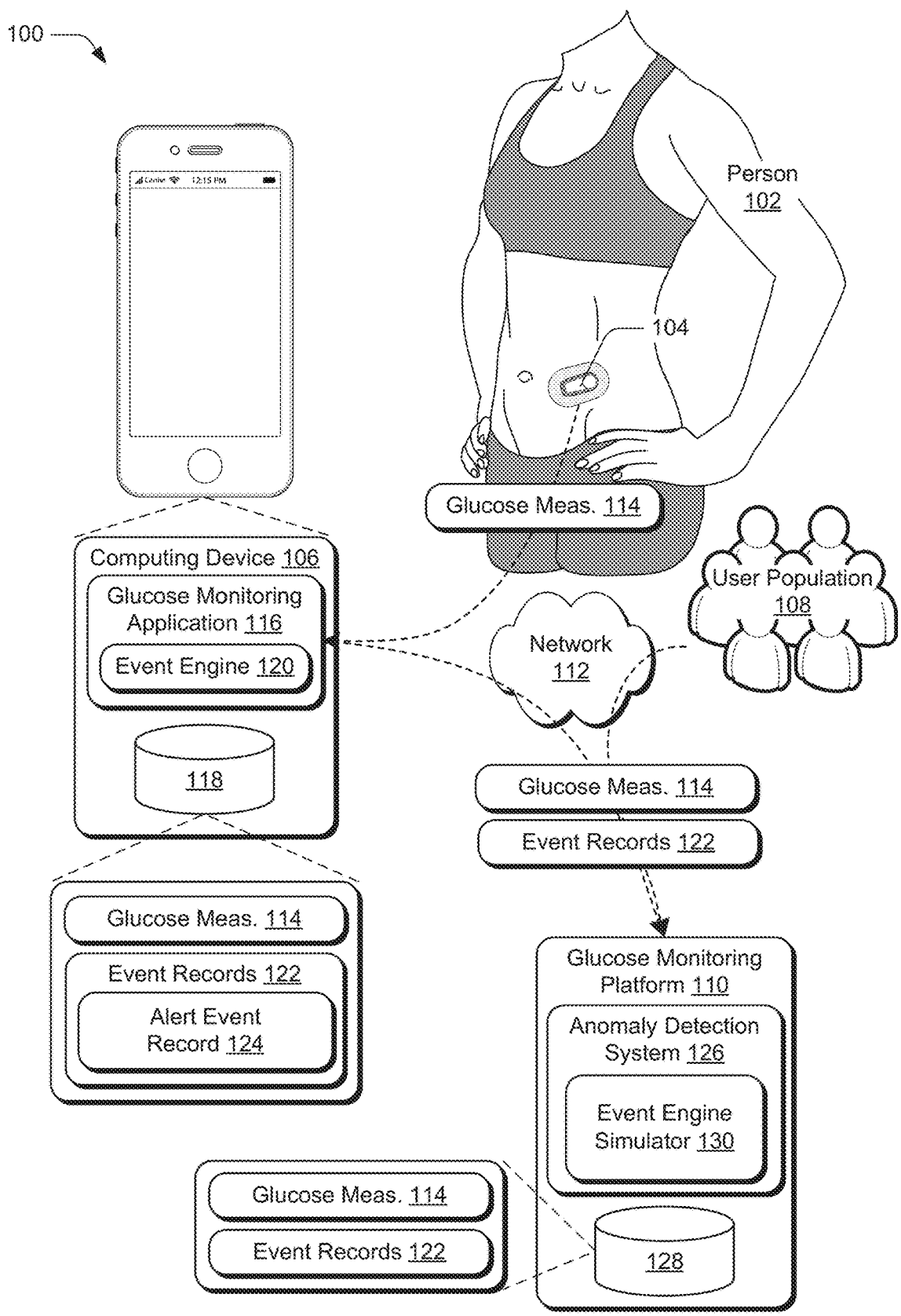
FIG. 1 is an illustration of an environment in an exemplary implementation that is operable to employ techniques described herein.

Detection of anomalous computing environment behavior using glucose is described. An anomaly detection system receives glucose measurements collected by wearable glucose monitoring devices and event records associated with the glucose measurements during a first time period. The glucose measurements and event records, for example, can be received from glucose monitoring applications, implemented at a plurality of computing devices. These computing devices obtain the glucose measurements from respective glucose monitoring devices that each collect glucose measurements of a user. In some cases, for example, the glucose monitoring device is a wearable glucose monitoring device that collects glucose measurements from the user at predetermined intervals in real-time, e.g., every five minutes.

An event engine of the glucose monitoring application is configured to process the glucose measurements to generate events associated with glucose monitoring, such as glycemic events (e.g., hyperglycemia and hypoglycemia), predicted glycemic events (e.g., upcoming low glucose or upcoming high glucose), and so on. The generated events may be output to the computing device of the user and also recorded in the event records, which maintain a listing of all the events generated by the event engine. By way of example, alerts and alarms may correspond to a type of event identified and recorded by the event engine. In general, alerts and alarms may be triggered for dangerous or potentially dangerous health conditions identified and recorded by the event engine, where the glucose monitoring application is configured to cause output of an alert or alarm (e.g., to notify the user of the condition) via the computing device or via some other device, responsive to identification of such event.

In operation, the wearable glucose monitoring device may be configured to transmit the glucose measurements to the computing device substantially at a predetermined time interval, e.g., one measurement every five minutes. Despite configuration generally to transmit the measurements at a predetermined time interval, the glucose monitoring application, and thus the event engine, may not receive one or more of those measurements at their scheduled transmission time for various reasons, e.g., one or more measurements may not be received at their scheduled time (but instead received later) due to signal loss between the computing device and the wearable glucose monitoring device. In scenarios where the event engine does not receive those glucose measurements as scheduled, the event engine may not generate certain events, e.g., may not generate an alert or an alarm when measurements corresponding to a glycemic event (e.g., hypo- or hyper-glycemia) are not received on schedule. When an event is not generated by the event engine and output by the glucose monitoring application, the event engine also does not cause the event to be recorded in the event records. Accordingly, such an event may be "missed" by the event engine and "missing" from the event records. Although signal loss is discussed as one cause of missing events, the event engine may miss events for various other reasons without departing from the spirit or scope of the described techniques, which may in some cases be due to competition for resources of the computing device.

Conventionally, such missing events can only be detected when a critical mass of users complain about missing events. For example, users may notice that their glucose monitoring application is failing to output low glucose alerts, and thus contact the glucose monitoring system with a complaint. When enough complaints are received, an investigation may be initiated by application developers or customer service staff to determine a solution to the problem. This process, however, is slow and requires a critical number of users to detect the problem and voice the complaint. Particularly in cases where missed events can be harmful or even life threatening to users, it is important to detect missing events as early as possible. Moreover, often times missing events related to low glucose may not even be noticed by users, such as when those events are missed while the user is sleeping.

Thus, to solve this problem of conventional systems, missing events that are missing from the event records during a first time period are identified by processing the glucose measurements using an event engine simulator that is a replication of the event engine. The event engine simulator may be implemented using the same or similar logic (or a portion of the same or similar logic) as the event engine of the glucose monitoring application. For example, the event engine simulator may be implemented using at least some of the same or similar source code as the event engine. The event engine simulator receives the same glucose measurements as the event engine, and generates simulated events. The simulated events are then compared to actual events in the event records during the first time period in order to identify the events which are missing from the event records. The missing events, therefore, correspond to simulated events which do not have a matching actual event in the event records during the first time period.

The anomaly detection system may then determine whether missing events for a second time period are anomalous in view of historical missing events determined for the first time period that precedes the second time period. To do so, an anomaly detection model is generated based on the missing events identified during the first time period. For example, the anomaly detection model may be generated based on missing events identified during a first time period spanning eight weeks, and the model may then be used to detect anomalous behavior in a second time period spanning one week. The anomaly detection model includes a predicted range of missing events during the second time period that is non-anomalous.

In a manner that is similar to identifying missing events during the first time period, the anomaly detection system receives additional glucose measurements collected by the wearable glucose monitoring device and event records associated with the additional glucose measurements during the second time period. Missing events that are missing from the event records during the second time are identified by processing the additional glucose measurements using the event engine simulator. For example, the event engine simulator receives the same glucose measurements as the event engine during the second time period, and generates simulated events. The simulated events are then compared to actual events in the event records during the second time period in order to identify the missing events.

Anomalous behavior is then detected if the identified missing events during the second time period are outside the predicted range of missing events of the anomaly detection model. Over a population of thousands or even millions of users, for example, a certain number of missing events is to be expected. Anomalous events, therefore, are detected when the number of missing events are outside the predicted range of missing events of the anomaly detection model. By way of example, if the predicted range of missing events defined by the anomaly detection model is 10-30 missing events per day, then anomalous behavior would be identified, for a given day, if the number of missing events is 40, thereby exceeding the upper threshold of the predicted range of 30 missing events. In contrast, if 20 missing events are identified for a given day, then anomalous behavior would not be detected because 20 missing events is within the predicted range of missing events for that day. In accordance with the described techniques, ranges may also or alternatively be described in terms of percentages, e.g., percentages of all the events over the user population.

Thus, the described techniques discussed herein solve many of the problems of conventional systems by automatically detecting anomalous behavior early on. That is, rather than relying on a critical mass of user complaints in order to detect an issue causing missing events, the described techniques simulate events (e.g., daily) in order to detect missing events which may correspond to anomalous behavior. Notably, by modeling the behavior of missing events over a previous time period, the system tolerates a certain number of missing events each day which are within the normal range of missing events. However, if the number of missing events are outside the predicted range, then the anomalous behavior is quickly identified and can be acted on before the issue causing missing events causes many more missed events for users. Thus, the ability to quickly identify anomalous behavior enables issues causing the anomalous behavior to be quickly solved, which decreases the number of health-related issues for users that rely on glucose monitoring applications.

In the following discussion, an exemplary environment is first described that may employ the techniques described herein. Examples of implementation details and procedures are then described which may be performed in the exemplary environment as well as other environments. Performance of the exemplary procedures is not limited to the exemplary environment and the exemplary environment is not limited to performance of the exemplary procedures.

Example of an Environment

FIG. 1 is an illustration of an environment 100 in an example implementation that is operable to employ detection of anomalous computing environment behavior using glucose as described herein. The illustrated environment 100 includes person 102, who is depicted wearing a wearable glucose monitoring device 104. The illustrated environment 100 also includes computing device 106, other users in a user population 108 that wear glucose monitoring devices 104, and glucose monitoring platform 110. The wearable glucose monitoring device 104, computing device 106, user population 108, and glucose monitoring platform 110 are communicatively coupled, including via a network 112.

Alternatively or additionally, the wearable glucose monitoring device 104 and the computing device 106 may be communicatively coupled in other ways, such as using one or more wireless communication protocols or techniques. By way of example, the wearable glucose monitoring device 104 and the computing device 106 may communicate with one another using one or more of Bluetooth (e.g., Bluetooth Low Energy links), near-field communication (NFC), 5G, and so forth.

In accordance with the described techniques, the wearable glucose monitoring device 104 is configured to provide measurements of the person 102's glucose. Although a wearable glucose monitoring device is discussed herein, it is to be appreciated that anomalous computing environment behavior may be detected using glucose in connection with other devices capable of providing glucose measurements, e.g., non-wearable glucose devices (such as blood glucose meters requiring finger sticks), patches, and so forth. In implementations that involve the wearable glucose monitoring device 104, though, it may be configured with a glucose sensor that continuously detects analytes indicative of the person 102's glucose and enables generation of glucose measurements. In the illustrated environment 100 and throughout the detailed description these measurements are represented as glucose measurements 114.

In one or more implementations, the wearable glucose monitoring device 104 is a continuous glucose monitoring ("CGM") system. As used herein, the term "continuous" used in connection with glucose monitoring may refer to an ability of a device to produce measurements substantially continuously, such that the device may be configured to produce the glucose measurements 114 at intervals of time (e.g., every hour, every 30 minutes, every 5 minutes, and so forth), responsive to establishing a communicative coupling with a different device (e.g., when the computing device 106 establishes a wireless connection with the wearable glucose monitoring device 104 to retrieve one or more of the measurements), and so forth This functionality along with further aspects of the wearable glucose monitoring device 104's configuration are discussed in more detail in relation to FIG. 2.

Additionally, the wearable glucose monitoring device 104 transmits the glucose measurements 114 to the computing device 106, such as via a wireless connection. The wearable glucose monitoring device 104 may communicate these measurements in real-time, e.g., as they are produced using a glucose sensor. Alternately or in addition, the wearable glucose monitoring device 104 may communicate the glucose measurements 114 to the computing device 106 at set time intervals. For example, the wearable glucose monitoring device 104 may be configured to communicate the glucose measurements 114 to the computing device 106 every five minutes (as they are being produced). Certainly, an interval at which the glucose measurements 114 are communicated may be different from the examples above without departing from the spirit or scope of the described techniques. The measurements may be communicated by the wearable glucose monitoring device 104 to the computing device 106 according to other bases in accordance with the described techniques, such as based on a request from the computing device 106. Regardless, the computing device 106 may maintain the glucose measurements 114 of the person 102 at least temporarily, e.g., in computer-readable storage media of the computing device 106.

In addition to the glucose measurements 114, the wearable glucose monitoring device 104 may produce and transmit supplemental sensor information (not shown) to the computing device 106, e.g., via the wireless connection. The wearable glucose monitoring device 104 may communicate this information with the glucose measurements 114, e.g., when the glucose measurements 114 are communicated, so is the supplemental sensor information. Alternatively or additionally, the wearable glucose monitoring device 104 may communicate the supplemental sensor information to the computing device 106 at set time intervals, which may or may not match when the glucose measurements 114 are communicated to the computing device 106. It is to be appreciated that the supplemental sensor information may be communicated to the computing device 106 according to a variety of other bases, which may or may not match when the glucose measurements 114 are communicated to the computing device 106, without departing from the spirit or scope of the described techniques.

The supplemental sensor information may correspond to various information that supplements the glucose measurements 114 in accordance with the described techniques. By way of example, the supplemental sensor information may include information describing a state of one or more sensors of the wearable glucose monitoring device 104, e.g., the state or states indicating whether the one or more sensors are operating within a threshold of normal (e.g., expected) operation and/or whether the one or more sensors are not operating normally. In addition to information describing sensor operation, the supplemental sensor information may describe operation and/or status of one or more other components of the wearable glucose monitoring device 104, such as a state of a battery, a state of a transmitter or receiver for sending and receiving communications, and information about communications transmitted and/or received, to name just a few. Additionally or alternatively, the supplemental sensor information may include notifications (e.g., alerts and/or alarms) triggered by onboard logic (e.g., implemented in hardware, firmware, and or software) of the wearable glucose monitoring device 104 based on the glucose measurements 114 produced by the wearable glucose monitoring device 104. Such supplemental sensor information may describe a variety of other aspects related to the glucose measurements 114 and operation of the wearable glucose monitoring device 104 without departing from the spirit or scope of the described techniques.

Although illustrated as a mobile device (e.g., a mobile phone), the computing device 106 may be configured in a variety of ways without departing from the spirit or scope of the described techniques. By way of example and not limitation, the computing device 106 may be configured as a different type of mobile device (e.g., a wearable device or tablet device), a desktop computer, or a laptop computer, just to name a few form factors. In one or more implementations, the computing device 106 may be configured as a dedicated device associated with the glucose monitoring platform 110, e.g., with functionality to obtain the glucose measurements 114 from the wearable glucose monitoring device 104, perform various computations in relation to the glucose measurements 114, display information related to the glucose measurements 114 and the glucose monitoring platform 110, communicate the glucose measurements 114 to the glucose monitoring platform 110, and so forth.

Additionally, the computing device 106 may be representative of more than one device in accordance with the described techniques. In one or more scenarios, for instance, the computing device 106 may correspond to both a wearable device (e.g., a smart watch) and a mobile phone. In such scenarios, both of these devices may be capable of performing at least some of the same operations, such as to receive the glucose measurements 114 from the wearable glucose monitoring device 104, communicate them via the network 112 to the glucose monitoring platform 110, display information related to the glucose measurements 114, and so forth. Alternatively or in addition, different devices may have different capabilities that other devices do not have or that are limited through computing instructions to specified devices.

In the scenario where the computing device 106 corresponds to a separate smart watch and a mobile phone, for instance, the smart watch may be configured with various sensors and functionality to measure a variety of physiological markers (e.g., heartrate, heartrate variability, breathing, rate of blood flow, and so on) and activities (e.g., steps or other exercise) of the person 102. In this scenario, the mobile phone may not be configured with these sensors and functionality, or it may include a limited amount of that functionality—although in other scenarios a mobile phone may be able to provide the same functionality. Continuing with this particular scenario, the mobile phone may have capabilities that the smart watch does not have, such as a camera to capture images associated with glucose monitoring and an amount of computing resources (e.g., battery and processing speed) that enables the mobile phone to more efficiently carry out computations in relation to the glucose measurements 114. Even in scenarios where a smart watch is capable of carrying out such computations, computing instructions may limit performance of those computations to the mobile phone so as not to burden both devices and to utilize available resources efficiently. To this extent, the computing device 106 may be configured in different ways and represent different numbers of devices than discussed herein without departing from the spirit and scope of the described techniques.

In accordance with the discussed techniques, the computing device 106 includes glucose monitoring application 116. In general, the glucose monitoring application 116 is configured to perform a variety of activities related to monitoring glucose. Examples of these activities include, but are not limited to, preparing the wearable glucose monitoring device 104 for insertion and production of the glucose measurements 114 (e.g., via exchange of various electronic communications), obtaining the glucose measurements 114 and the supplemental sensor information from the wearable glucose monitoring device 104, monitoring the operational health of the glucose monitoring device 104, causing output (e.g., display) of user interfaces via the computing device 106 to present information about monitored glucose (e.g., a plot of the person 102's glucose measurements 114 over time), and causing output of user interfaces or user interface elements via the computing device 106 to present decision support information (e.g., a digital coach, social features related to glucose monitoring and management, educational information, and so forth), to name just a few.

In one or more implementations, the glucose monitoring application 116 is configured to process the glucose measurements 114 to identify events associated with glucose monitoring, such as glycemic events (e.g., hyperglycemia and hypoglycemia), predicted glycemic events (e.g., upcoming low glucose or upcoming high glucose), and so on. To process the glucose measurements 114 and identify such events, the glucose monitoring application 116 may leverage event engine 120. The event engine 120 may receive the glucose measurements 114 as input, process those measurements according to underlying logic (e.g., heuristic rules, one or more machine learning models, and/or threshold comparison), and, when an event is identified according to the processing, output an indication indicative of the identified event. Responsive to the event engine 120 outputting an event, the event engine 120 and/or the glucose monitoring application 116 may record the event in event records 122.

By way of example, alerts and alarms may correspond to one or more types of events identified by the event engine 120 and output for recording in the event records 122. In general, alerts and alarms may be triggered for dangerous or potentially dangerous health conditions identified and output for recording by the event engine 120. In connection with the event engine 120 outputting an alert- or alarm-event, the glucose monitoring application 116 may be configured to cause output of an alert or alarm signal (e.g., to notify the user of the condition) via the computing device 106 or via some other device. An alert or alarm signal may be output via a display (e.g., via a display device of the computing device 106), via an audible component, and/or via a haptic feedback component, to name just a few. Alert event record 124 may correspond to one record of a plurality of records forming the event records 122 and may be configured to persist the alert- and alarm-events identified and output by the event engine 120. In accordance with the described techniques, the alert event record 124 comprises a log of alerts and/or alarms triggered by the event engine 120 and entered in the alert event record 124. In accordance with the described techniques, a given alert or alarm triggered by the event engine 120 may have a corresponding entry in the alert event record 124.

In the illustrated example, the computing device 106 includes storage device 118. The storage device 118 is depicted storing the glucose measurements 114 and the event records 122, including the alert event record 124. It is to be appreciated that the storage device 118 may store a variety of data associated with glucose monitoring without departing from the spirit or scope of the described techniques, such as the supplemental sensor information. Additionally, the storage device 118 may represent one or more databases and also other types of storage capable of storing the glucose measurements 114 and the event records 122.

In one or more implementations, the glucose monitoring application 116 may transmit the glucose measurements 114, the event records 122 (or a portion thereof), and other information (e.g., the supplemental sensor information) to the glucose monitoring platform 110. This may be referred to as "posting" information to the glucose monitoring platform 110. The glucose monitoring platform 110 may process and store the glucose measurements 114 and the event records 122 of the person 102 as well as the glucose measurements 114 and the event records 122 of users of the user population 108 in connection with a variety of functionality. In accordance with the described techniques, for example, the glucose monitoring platform 110 may leverage the glucose measurements 114 and the event records 122 of the person 102 and of the user population 108 to identify anomalous behavior with one or more computing environments, e.g., anomalous behavior of the glucose monitoring application 116 on a particular version of an operating system and/or a particular brand of mobile device.

The anomaly detection system 126 is configured to detect anomalous behavior by obtaining at least the glucose measurements 114 and the event records 122 and by processing them using one or more anomaly detection techniques. In one or more implementations, the glucose monitoring platform 110 stores the glucose measurements 114, the event records 122, and the supplemental sensor information of the person 102 and the user population 108 in storage device 128. Like the storage device 118, the storage device 128 may represent one or more databases and also other types of storage capable of storing such information. In connection with detecting anomalies, the anomaly detection system 126 may obtain one or more of the glucose measurements 114 and the event records 122 from the storage device 128. The anomaly detection system 126 may then detect anomalies, in part, by using event engine simulator 130.

In general, the event engine simulator 130 is a replication of the event engine 120. As used herein, the term "replication" refers to a configuration that enables the event engine simulator 130, in response to receiving the same glucose measurements 114 as the event engine 120, to generate simulated events in scenarios where the event engine 120 is configured to generate events. In a scenario where a particular sequence of glucose measurements indicates an upcoming adverse health condition and where the event engine 120 is configured to generate an event (e.g., an alert) responsive to receiving the particular sequence of glucose measurements as input, for example, the event engine simulator 130 is configured to generate a simulated event (e.g., an alert) responsive to receiving the particular sequence of glucose measurements as input. To the extent that event engine 120 may be configured to generate events for different scenarios related to glucose monitoring (e.g., in addition to alerts and alarms), the event engine simulator 130 may also be configured to generate simulated events for such different scenarios.

In order to simulate the events generated by the event engine 120, the event engine simulator 130 may be implemented using the same or similar logic (or a portion of the same or similar logic). By way of example and not limitation, the event engine simulator 130 may be implemented using at least some of the same or similar source code as the event engine 120, at least some of the same or similar executable code as the event engine 120, at least some of the same or similar set of rules used by the event engine 120, at least some of the same or similar models (e.g., machine learning models) used by the event engine 120, and so forth. It is to be appreciated that the event engine simulator 130 may be configured in a variety of ways to imitate the processing and output of the event engine 120—to simulate behavior of the event engine 120—without departing from the spirit or scope of the described techniques.

In contrast to the event engine 120, however, the event engine simulator 130 may operate in a controlled simulation environment, e.g., at the glucose monitoring platform 110 and during scheduled simulations (e.g., daily) rather than in real-time as part of the computing device 106 where the glucose monitoring application 116 may "compete" with other applications of the computing device 106 for computing resources. The event engine 120, for instance, may be configured to process the glucose measurements 114 of the person 102 as they are received from the wearable glucose monitoring device 104. In operation, the wearable glucose monitoring device 104 may be configured to transmit the glucose measurements 114 to the computing device 106 substantially at a predetermined time interval, e.g., one measurement every five minutes. Despite configuration generally to transmit the measurements at a predetermined time interval, the glucose monitoring application 116, and thus the event engine 120, may not receive one or more of those measurements at their scheduled transmission time for various reasons, e.g., one or more measurements may not be received at their scheduled time (but instead received later) due to signal loss between the computing device 106 and the wearable glucose monitoring device 104. In scenarios where the event engine 120 does not receive those glucose measurements 114 as scheduled, the event engine 120 may not generate certain events, e.g., may not generate an alert or an alarm when measurements corresponding to a glycemic event (e.g., hypo- or hyper-glycemia) are not received on schedule. When an event is not generated or otherwise output by the event engine 120, the event engine 120 also may not cause the event to be recorded in the event records 122. Accordingly, such an event may be "missed" by the event engine 120 and "missing" from the event records 122.

Although signal loss is discussed as one cause of missing events, the event engine 120 may miss events for various other reasons without departing from the spirit or scope, which may in some cases be due to competition for resources of the computing device 106. For example, an operating system of the computing device 106 may cause the glucose monitoring application 116 to be run in a background to one or more other applications, such that the one or more other applications have priority to the computing resources of the computing device 106. Alternatively or in addition, an operating system of the computing device 106 may, during operation, prevent an event output by the event engine from being recorded in the event records 122. Alternatively or additionally, a provider of the computing device 106's operating system may change a manner in which resources are allocated between versions of the operating system. As a result, the glucose monitoring application 116 may not be configured, as deployed, to access those resource in a manner that keeps the event engine 120 processing the glucose measurements 114 at every single scheduled transmission time. The event engine 120 may also miss events due to user actions, such as user actions to close the glucose monitoring application 116, to turn off or restart the computing device 106, to turn off communicable couplings (e.g., a Bluetooth or other wireless coupling with the wearable glucose monitoring device 104), and so on. The event engine 120 may also miss events due to failures of the computing device 106's computing environment generally, such as crashes, stalls, corruptions to executable code or memory, malware, and so forth. It is to be appreciated that the above discussed reasons are just a few of reasons that the event engine 120 may miss events and further appreciated that the event engine 120 may miss events for different reasons without departing from the spirit or scope of the described techniques.

The event ending 120's deployment as part of the environment of the computing device 106, to process data related to glucose monitoring as it is received while also competing with other applications for the resources of the computing device 106, contrasts with operation of the event engine simulator 130. For instance, the environment in which the event engine simulator 130 is deployed may be generally controlled (e.g., by the anomaly detection system 126) to eliminate sources of missed events in connection with simulation. As one example, rather than receiving data as it is produced and communicated by the wearable glucose monitoring device 104 of the person 102, the event engine simulator 130 can obtain data from the storage device 128 for the person 102 and also for users of the user population 108, which can number in the thousands, hundreds of thousands, millions, or more. Moreover, the event engine simulator 130 may be configured to access large amounts of historical data from the storage device 128 for a simulation, e.g., a last nine weeks of data of the person 102 and the user population 108. Further still, before data is provided to the event engine simulator 130, missing data may be interpolated and incorporated so that complete sequences of the data, e.g., of glucose measurements 114, for the respective time period are provided as input to the event engine simulator 130.

In addition, the anomaly detection system 126 may cause computing resources (e.g., processing cycles, memory, and so forth) to be dedicated to the event engine simulator 130 while it simulates events, e.g., while it processes the glucose measurements 114 of the person 102 and the user population 108 to identify glucose-related events for the person 102 and the user population 108. Through control of the simulation environment, the anomaly detection system 126 enables the event engine simulator 130 to generate simulated events for the actual events generated by the event engine 120 and also for the events missed by the event engine 120. The missed events may be determined by comparing the events simulated by the event engine simulator 130 to the actual events generated by the event engine 120 and also recorded in the event records 122. As discussed in more detail below, the anomaly detection system 126 may then determine whether the missing events determined for a given time period are anomalous in view of historical missing events determined for a preceding time period. In the context of measuring glucose, e.g., continuously, and obtaining data describing such measurements, consider the following discussion of FIG. 2.

Figure 2:
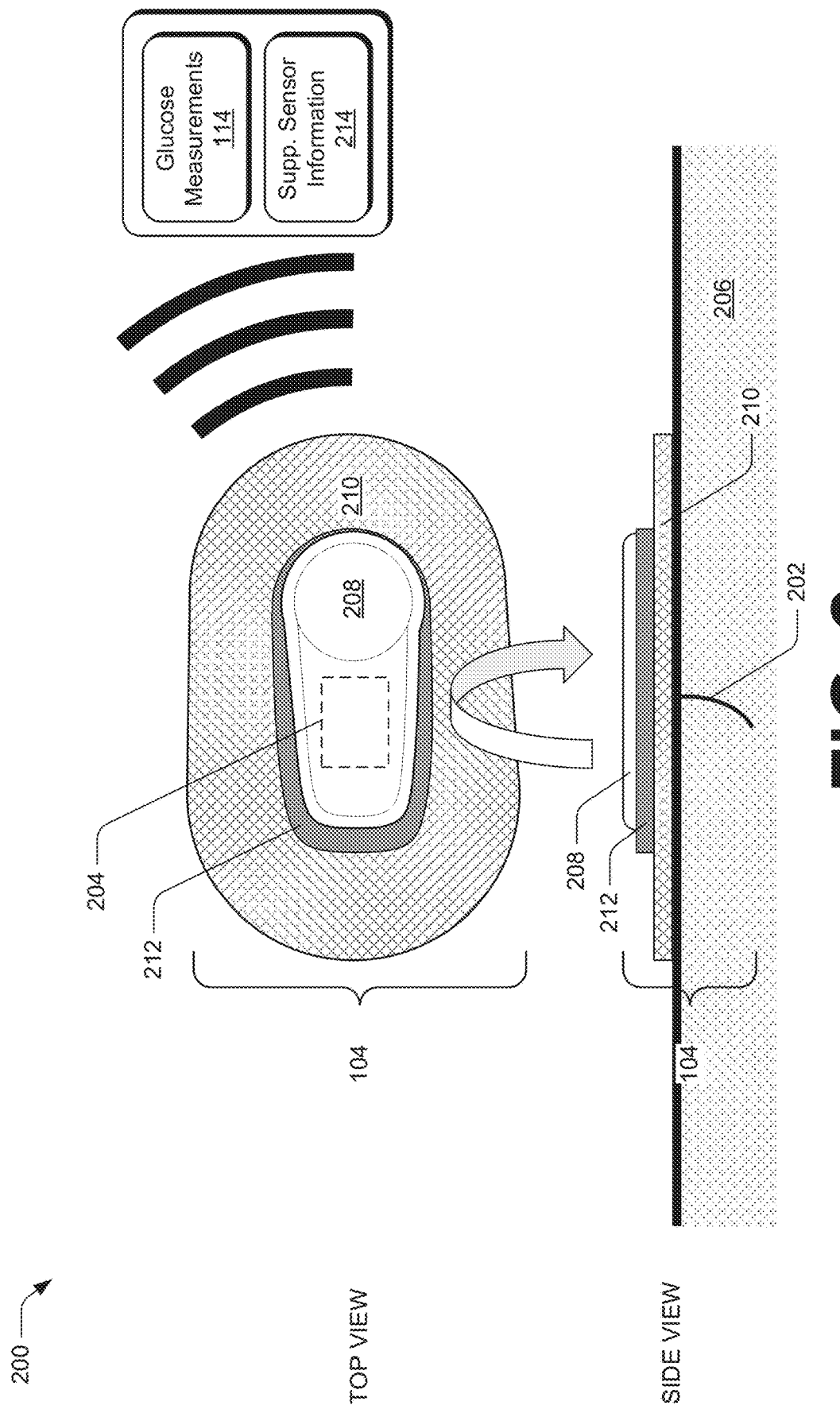
FIG. 2 depicts an example of the wearable glucose monitoring device of FIG. 1 in greater detail.

FIG. 2 depicts an example 200 of an implementation of the wearable glucose monitoring device 104 of FIG. 1 in greater detail. In particular, the illustrated example 200 includes a top view and a corresponding side view of the wearable glucose monitoring device 104. It is to be appreciated that the wearable glucose monitoring device 104 may vary in implementation from the following discussion in various ways without departing from the spirit or scope of the described techniques. As noted above, for instance, anomalous computing environment behavior may be detected using glucose in connection with other types of devices for glucose monitoring, such as non-wearable devices (e.g., blood glucose meters requiring finger sticks), patches, and so forth.

In this example 200, the wearable glucose monitoring device 104 is illustrated to include a sensor 202 and a sensor module 204. Here, the sensor 202 is depicted in the side view having been inserted subcutaneously into skin 206, e.g., of the person 102. The sensor module 204 is depicted in the top view as a dashed rectangle. The wearable glucose monitoring device 104 also includes a transmitter 208 in the illustrated example 200. Use of the dashed rectangle for the sensor module 204 indicates that it may be housed or otherwise implemented within a housing of the transmitter 208. In this example 200, the wearable glucose monitoring device 104 further includes adhesive pad 210 and attachment mechanism 212.

In operation, the sensor 202, the adhesive pad 210, and the attachment mechanism 212 may be assembled to form an application assembly, where the application assembly is configured to be applied to the skin 206 so that the sensor 202 is subcutaneously inserted as depicted. In such scenarios, the transmitter 208 may be attached to the assembly after application to the skin 206 via the attachment mechanism 212. Alternatively, the transmitter 208 may be incorporated as part of the application assembly, such that the sensor 202, the adhesive pad 210, the attachment mechanism 212, and the transmitter 208 (with the sensor module 204) can all be applied at once to the skin 206. In one or more implementations, this application assembly is applied to the skin 206 using a separate sensor applicator (not shown). Unlike the finger sticks required by conventional blood glucose meters, the user initiated application of the wearable glucose monitoring device 104 is nearly painless and does not require the withdrawal of blood. Moreover, the automatic sensor applicator generally enables the person 102 to embed the sensor 202 subcutaneously into the skin 206 without the assistance of a clinician or healthcare provider.

The application assembly may also be removed by peeling the adhesive pad 210 from the skin 206. It is to be appreciated that the wearable glucose monitoring device 104 and its various components as illustrated are simply one example form factor, and the wearable glucose monitoring device 104 and its components may have different form factors without departing from the spirit or scope of the described techniques.

In operation, the sensor 202 is communicatively coupled to the sensor module 204 via at least one communication channel which can be a wireless connection or a wired connection. Communications from the sensor 202 to the sensor module 204 or from the sensor module 204 to the sensor 202 can be implemented actively or passively and these communications can be continuous (e.g., analog) or discrete (e.g., digital).

The sensor 202 may be a device, a molecule, and/or a chemical which changes or causes a change in response to an event which is at least partially independent of the sensor 202. The sensor module 204 is implemented to receive indications of changes to the sensor 202 or caused by the sensor 202. For example, the sensor 202 can include glucose oxidase which reacts with glucose and oxygen to form hydrogen peroxide that is electrochemically detectable by the sensor module 204 which may include an electrode. In this example, the sensor 202 may be configured as or include a glucose sensor configured to detect analytes in blood or interstitial fluid that are indicative of glucose level using one or more measurement techniques. In one or more implementations, the sensor 202 may also be configured to detect analytes in the blood or the interstitial fluid that are indicative of other markers, such as lactate levels, which may improve accuracy in identifying or predicting glucose-based events. Additionally or alternately, the wearable glucose monitoring device 104 may include additional sensors to the sensor 202 to detect those analytes indicative of the other markers.

In another example, the sensor 202 (or an additional sensor of the wearable glucose monitoring device 104—not shown) can include a first and second electrical conductor and the sensor module 204 can electrically detect changes in electric potential across the first and second electrical conductor of the sensor 202. In this example, the sensor module 204 and the sensor 202 are configured as a thermocouple such that the changes in electric potential correspond to temperature changes. In some examples, the sensor module 204 and the sensor 202 are configured to detect a single analyte, e.g., glucose. In other examples, the sensor module 204 and the sensor 202 are configured to detect multiple analytes, e.g., sodium, potassium, carbon dioxide, and glucose. Alternately or additionally, the wearable glucose monitoring device 104 includes multiple sensors to detect not only one or more analytes (e.g., sodium, potassium, carbon dioxide, glucose, and insulin) but also one or more environmental conditions (e.g., temperature). Thus, the sensor module 204 and the sensor 202 (as well as any additional sensors) may detect the presence of one or more analytes, the absence of one or more analytes, and/or changes in one or more environmental conditions.

In one or more implementations, the sensor module 204 may include a processor and memory (not shown). The sensor module 204, by leveraging the processor, may generate the glucose measurements 114 based on the communications with the sensor 202 that are indicative of the above-discussed changes. Based on these communications from the sensor 202, the sensor module 204 is further configured to generate communicable packages of data that include at least one glucose measurement 114. In one or more implementations, the sensor module 204 may configure those packages to include additional data, including, by way of example and not limitation, supplemental sensor information 214, which may correspond to the supplemental sensor information discussed in relation to FIG. 1 but not shown. Such supplemental sensor information may include any combination of the information discussed in relation to FIG. 1, a sensor identifier, a sensor status, temperatures that correspond to the glucose measurements 114, measurements of other analytes that correspond to the glucose measurements 114, and so forth. It is to be appreciated that supplemental sensor information 214 may include a variety of data that supplements at least one glucose measurement 114 without departing from the spirit or scope of the described techniques.

In implementations where the wearable glucose monitoring device 104 is configured for wireless transmission, the transmitter 208 may transmit the glucose measurements 114 and/or the supplemental sensor information 214 wirelessly as a stream of data to a computing device. Alternately or additionally, the sensor module 204 may buffer the glucose measurements 114 and/or the supplemental sensor information 214 (e.g., in memory of the sensor module 204 and/or other physical computer-readable storage media of the wearable glucose monitoring device 104) and cause the transmitter 208 to transmit the buffered glucose measurements 114 and/or buffered supplemental sensor information 214 later at various intervals, e.g., time intervals (every second, every thirty seconds, every minute, every five minutes, every hour, and so on), storage intervals (when the buffered glucose measurements 114 and/or supplemental sensor information 214 reach a threshold amount of data or a number of measurements), and so forth.

Having considered an example of an environment and an example of a wearable glucose monitoring device, consider now a discussion of some examples of details of the techniques for detection of anomalous computing environment behavior using glucose in accordance with one or more implementations.

Detecting Anomalous Computing Environment Behavior Using Glucose

Figure 3:
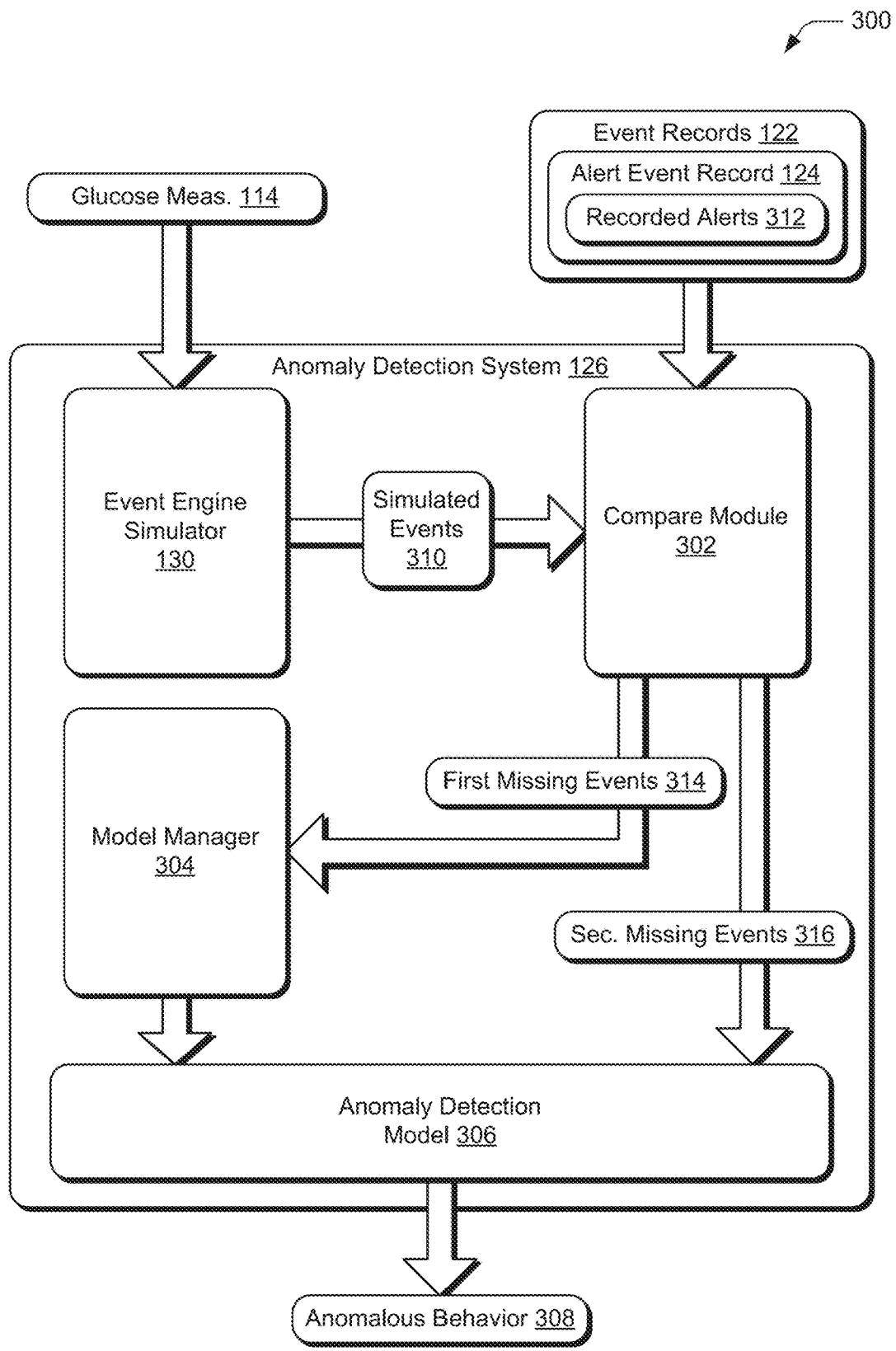
FIG. 3 depicts an example of a system in which the anomaly detection system of FIG. 1 detects anomalous behavior of a computing environment by simulating events.

FIG. 3 depicts an example 300 of a system in which an anomaly detection system of FIG. 1 detects anomalous behavior of a computing environment by simulating events. The illustrated example 300 includes from FIG. 1 the anomaly detection system 126 having the event engine simulator 130 and is shown receiving the glucose measurements 114 and the event records 122 as input.

In the illustrated example 300, the anomaly detection system 126 further includes compare module 302, model manager 304, and anomaly detection model 306 to detect anomalous behavior 308 of a computing environment. Although the anomaly detection system 126 is depicted with these various components, it is to be appreciated that in implementations the anomaly detection system 126 may include fewer, more, and/or different components without departing from the spirit or scope of the described techniques.

In accordance with the described techniques, the event engine simulator 130 is configured to generate simulated events 310. In this example 300, the event engine simulator 130 is depicted receiving the glucose measurements 114 as input, although the event engine simulator 130 may receive additional or different data as input to generate the simulated events 310 in one or more implementations. For example, the event engine simulator 130 may additionally or alternatively receive the supplemental sensor information 214 and/or other information (e.g., health tracking information, application usage data, user profile information) to generate the simulated events 310.

Regardless, the event engine simulator 130 is configured in one or more implementations to process the glucose measurements 114 and generate the simulated events 310 based on processing the glucose measurements 114. In accordance with the described techniques, the event engine simulator 130 may in operation obtain the glucose measurements 114 for the person 102 and the user population 108 or a subset of the user population 108. For example, the event engine simulator 130 may obtain the glucose measurements 114 for a subset of the user population 108 matching specified criteria. Such criteria may include, by way of example and not limitation, a type of computing device on which the glucose monitoring application 116 operates (e.g., a mobile phone, a smart watch, a tablet, a dedicated glucose monitoring device, and so on), a manufacturer and/or model of computing device on which the glucose monitoring application 116 operates (e.g., Apple® iPhone 12, Samsung® Galaxy, Google® Pixel Phone 5, and so on), an operating system of the computing device on which the glucose monitoring application 116 operates (e.g., iOS, Android, and so on), a version of the operating system, a type of communicable coupling with a wearable glucose monitoring device 104 (e.g., Bluetooth, 5G, NFC, and so on), a status of the communicable coupling with a wearable glucose monitoring device 104, identity of servers that provide one or more services (e.g., of the glucose monitoring platform 110) to the glucose monitoring application 116 over the network 112, a status of servers that provide the one or more services to the glucose monitoring application 116, identifiers of hardware associated with the computing device 106 (e.g., onboard and/or communicably coupled), identifiers of software of the computing device 106 (e.g., including other applications), a make and/or model of the glucose monitoring device (e.g., Dexcom® G5, Dexcom® G6, Dexcom® G7, Abbott® Freestyle Libre, Abbott® Freestyle Libre 2), manufacturing lots of the glucose monitoring device (or components of the glucose monitoring device), user demographics, user locations, a version of the glucose monitoring application 116, and so forth. Accordingly, it is to be appreciated that the event engine simulator 130 may obtain data for a subset of the user population 108 that is selected based on specification of one or more of a variety of criteria without departing from the spirit or scope of the described techniques.

As mentioned above, the event engine simulator 130 is configured to process the glucose measurements 114 to identify or predict a glucose-related event in the glucose and to output a simulated event 310 responsive to identification or prediction of the glucose-related event. In accordance with the described techniques, the event engine simulator 130 is configured to identify or predict an event and output a simulated event 310 based on processing a sequence of glucose measurements 114 for which the event engine 120 is configured to identify or predict an event and record the event in the event records 122. This ability of the event engine simulator 130 to imitate, i.e., to simulate, the event engine 120 is based on configuration of the event engine simulator 130 that enables it to simulate the event engine 120 for one or more types of records—the event engine simulator 130 may be configured in some implementations to simulate the event engine 120's ability to generate simulated alert events but not simulated snooze-related events. As discussed above in relation to the illustrated example 100, for instance, the event engine simulator 130 may be configured to simulate the event engine based on implementation using at least some of the same or similar source code as the event engine 120, at least some of the same or similar executable code as the event engine 120, at least some of the same or similar set of rules used by the event engine 120, at least some of the same or similar models (e.g., machine learning models) used by the event engine 120, and so forth.

It is to be appreciated that the configuration of the event engine simulator 130 may be updated over time to enable the event engine simulator 130 to simulate more and more of the behavior of the event engine 120, e.g., to generate simulated events 310 for more and more of the events generated by the event engine 120.

It is to be appreciated, though, that in one or more implementations the event engine simulator 130 simply may be configured not to generate simulated events 310 for all event types for which the event engine 120 is configured to generate events. Alternatively or in addition, the event engine simulator 130 may be configured to generate simulated events 310 for only one or more specified types of events and not unspecified types of events. Simulated event generation may be limited in these ways because users of the anomaly detection system 126 (e.g., developers associated with the glucose monitoring platform 110) may have little, if any, utility for one or more of the events (or types of the events) generated by the event engine 120. Additionally, simulating all of the events that the event engine 120 is configured to generate events for, during a simulation involving data from the user population 108 (or even a subset of the user population 108), may require an amount of computing resources (e.g., processing cycles and/or memory) that hinders provision of other services of the glucose monitoring platform 110 and/or that costs more than a business associated with the glucose monitoring platform 110 is willing to spend.

In any case, the event engine simulator 130 may process the glucose measurements 114 to identify a variety of events and generate respective simulated events 310 responsive to the identification. The simulated events 310 may then be compared to actual events generated by the event engine 120 and recorded in the event records 122 in order to determine "missing events" from the event records 122. The anomaly detection model 306 may then process those missing events to determine whether the missing events determined for a given time period are anomalous relative to historical missing events.

As one example, the event engine simulator 130 is configured, in one or more implementations, to generate the simulated events 310 to simulate alerts and alarms generated by the event engine 120, e.g., so that anomalous behavior 308, if any, in relation to alerts and alarms can be determined for a given time period. As noted above, the actual events generated and recorded by the event engine 120 are persisted in the event records, such that alerts and alarms generated and recorded by the event engine 120 are persisted in the alert event record 124. In this example 300, the alerts and alarms actually recorded in the alert event record 124 are depicted as recorded alerts 312. It is to be appreciated that the glucose measurements 114, the event records 122, the alert event record 124, and the recorded alerts 312, depicted in this example 300 may correspond to the data from each user of the user population 108 that is being considered for a given simulation. In other words, the event engine simulator 130 may receive glucose measurements 114 for each user that is considered in connection with the given simulation, and the compare module 302 may receive an alert event record 124 for each user that is considered in connection with the given simulation.

Generally speaking, the compare module 302 compares the simulated events 310 to the recorded events to determine missing events. In the example where the simulated events 310 are generated for alerts and alarms, the compare module 302 is configured to compare the simulated events 310, indicative of the alerts and alarms that should have been generated by the event engine 120, to the recorded alerts 312—the alerts and alarms that were actually generated by the event engine 120 and recorded. The compare module 302 may compare the simulated events 310 to recorded events in a variety of ways without departing from the spirit or scope of the described techniques. By way of example and not limitation, the compare module 302 may extract a first event from the simulated events 310 and iterate over the events in the event records 122 to determine whether an actual event corresponding to the first event is included in the event records 122. If an actual event that corresponds to the first event is included in the event records, then the compare module 302 may proceed by extracting a second event from the simulated events 310 and iterating over the events in the event records 122 to determine whether an actual event corresponding to the second event is included in the event records.

However, if an actual event that corresponds to the first event is not included in the event records 122, then the compare module 302 may determine that the first event corresponds to a "missing event" from the event records 122. The compare module 302 may output the missing events or otherwise maintain a record of missing events, such as a counter that increments each time a missing event is determined, references (e.g., a list of identifiers) to each of the simulated events 310 that is determined to be missing from the event records 122, and/or a list of the determined missing events (e.g., which include details of the event similar to how an event is recorded by the event engine 120), to name just a few. The compare module 302 may process each of the simulated events 310 in a similar fashion to determine whether they are included in the event records 122 or not. The compare module 302 may compare the simulated events 310 to the event records 122 in other ways without departing from the spirit or scope of the described techniques. Continuing with the alerts and alarms example where the event engine simulator 130 generates simulated events 310 for alerts and alarms, for instance, the compare module 302 may simply compare a number of the simulated events 310 to a number of the recorded alerts 312 over a same time period. Alternately or additionally, the compare module 302 may use one or more sampling techniques to determine missing events.

As noted above, the compare module 302 is configured to output the missing events or some indication of the missing events, e.g., which may include or otherwise be associated with timestamps indicating an approximate time that the event engine 120 should have generated and/or recorded an event in the event records 122. In this example 300, the compare module 302 is depicted outputting first missing events 314 and second missing events 316, e.g., determined based on comparing the simulated events 310 to the recorded alerts 312. The first and second missing events 314, 316 may thus correspond to missing alerts and/or alarms in this example 300. In scenarios where the anomaly detection system 126 is determining anomalies for other types of events, the first and second missing events 314, 316 may correspond to events of those other types that are determined missing.

In accordance with the described techniques, the first missing events 314 may correspond to simulated events associated with times in a first time period and the second missing events 316 may correspond to simulated events associated with times in a second time period, where the first time period precedes the second time period. In one or more implementations, the glucose measurements 114 and the recorded events in the event records 122 may be configured as time-ordered data, e.g., they may be configured as time series data. Based on this, the simulated events 310 and the first and second missing events 314, 316 may also be configured as time-ordered data, e.g., time series. By time-ordered it is meant that the data (e.g., each measurement, event, and/or record) may be indexed or listed in time order or otherwise associated with a particular time (e.g., according to associated timestamps).

Regardless, the first missing events 314 may correspond to times that precede a point in time and the second missing events 316 may correspond to the point in time and/or times that are subsequent to the point in time. In one or more implementations, the point in time may correspond to a time in the past, e.g., not a current time at which the anomaly detection model 306 is actually used to process data to determine the anomalous behavior 308. By way of example, the anomaly detection system 126 may be deployed to detect the anomalous behavior 308 for a time-period-of-interest (e.g., a week) preceding a current time. In this example, the anomaly detection model 306 may further be configured to detect the anomalous behavior 308 for the time-period-of-interest based on a historical time period that precedes the time-period-of-interest, e.g., eight weeks that precede the week of interest. Accordingly, the point in time of this example—which is used to separate the first missing events 314 from the second missing events 316—may correspond to a week prior to a current time.

Given the example where the anomaly detection model 306 determines the anomalous behavior 308 for a preceding week based on eight weeks of events before that week, the first missing events 314 may correspond to weeks 2-9 and the second missing events 316 may correspond to week 1, where week 9 is the furthest week in the past from a current time and week 1 is the nearest week in the past from the current time. Certainly, although weeks of time are discussed in this example, the anomaly detection model 306 may be configured to determine the anomalous behavior 308 based on different periods of time, such as days (e.g., determining the anomalous behavior for a day from one or more historical days preceding that day), hours (e.g., determining the anomalous behavior for an hour from one or more historical hours preceding that hour), minutes, months, and quarters, to name just a few. The anomaly detection model 306 may determine the anomalous behavior 308 for a variety of time periods and from different amounts of time preceding such a time period (e.g., it is not limited to an 8 to 1 ratio) without departing from the spirit or scope of the described techniques.

In general, the model manager 304 is configured to generate or otherwise train the anomaly detection model 306. In particular, the model manager 304 may generate or otherwise train the anomaly detection model based on a first set of time-ordered historical data, e.g., the first missing events 314. Once the model manager 304 generates the anomaly detection model 306, the anomaly detection model 306 is configured to determine whether there are anomalies in a second set of time-ordered data, e.g., whether there are anomalies in the second missing events 316. In one or more implementations, the model manager 304 generates the anomaly detection model 306 based on the first set of historical data to model a predicted range of non-anomalous behavior. In the context of missing events, for example, the model manager 304 may generate the anomaly detection model 306 based on the first missing events 314 to model a predicted range of missing events (e.g., per day) that is non-anomalous.

As part of determining the anomalous behavior 308, the anomaly detection model 306 may process the second set of time-ordered data to determine which observed behaviors, as described by the second set of time-ordered data, fall within the anomaly detection model 306's predicted range and thus are not anomalous. The anomaly detection model 306 also determines which observed behaviors, as described by the second set of time-ordered data, fall outside the anomaly detection model 306's predicted range and thus are anomalous. The anomaly detection model 306 outputs the anomalous behavior 308 responsive to processing the data determined outside the predicted range. In the context of missing events, the missing events described by the second missing events 316 (e.g., a number or percent of missing events per day) that fall within the anomaly detection model 306's predicted range (e.g., configured also as a number or percent of missing events per day) are not anomalous. However, the missing events described by the second missing events 316 (e.g., a number or percent of missing events per day) that fall outside the anomaly detection model 306's predicted range (e.g., configured also as a number or percent of missing events per day) are anomalous. For these anomalous events, the anomaly detection model 306 outputs the anomalous behavior 308.

The model manager 304 may generate the anomaly detection model 306 according to a variety of algorithms. Although generation using time-ordered data (e.g., time-series data) is discussed above and below, the anomaly detection model 306 may in different implementations be implemented, at least in part, using an algorithm that leverages data that is not time-ordered. In at least one implementation that does involve time-ordered data, though, the model manager 304 may configure the anomaly detection model 306 as a Prophet model. In Prophet-model implementations, the model manager 304 may generate the anomaly detection model 306 such that, for example, seasonal features observed in the first set of data (e.g., the first missing events 314) are represented with Fourier series, holiday features (e.g., changes in behavior determined related to events like Thanksgiving) observed in the first set of data are represented with indicator features, and/or the model is fit using Markov Chain Monte Carlo sampling, to name just a few.

In general, Prophet models predict future uncertainty based on frequency and magnitude of change points, such that when there are change points that deviate from an "average" of the data frequently and or statistically significantly (e.g., in terms of magnitude), the predicted range is wider (e.g., less certain) than when there are fewer and less significant deviations. However, a relatively wider range may not enable the anomaly detection model 306 to detect, as anomalous, behaviors of the computing environment that may better be determined anomalous, such as behavior that can result in physical danger for users of the glucose monitoring application 116 and/or the wearable glucose monitoring device 104 (e.g., missed alerts and alarms). In one or more implementations, therefore, the anomaly detection model 306 may be modified from a base Prophet model implementation to narrow the predicted range, such as by setting a parameter of the model, corresponding to a future number of change points (e.g., a number of change points that will occur during the time period corresponding to the second set of data and beyond), to zero. Although anomalous behavior is discussed above and below as falling outside of a predicted range, in one or more implementations, the anomaly detection model 306 may detect anomalies in other ways, such as by detecting drift (e.g., upward or downward) in the data over time (even when the data continues to fall generally within the predicted range). It is to be appreciated that the model manager 304 may configure the anomaly detection model 306 to detect anomalies in a computing environment based on glucose and using any of a variety of anomaly detection techniques without departing from the spirit or scope of the described techniques.

In addition to missing events, the anomaly detection model 306 may be configured to output indications of the anomalous behavior 308 for a variety of metrics associated with the wearable glucose monitoring device 104, the glucose monitoring application 116, and/or the glucose monitoring platform 110. Examples of these other metrics include, by way of example and not limitation, glucose measurements (e.g., to detect drift over time or other anomalies that may arise due to changes in the computing environment and/or different configurations of the wearable glucose monitoring device 104), number of crashes (e.g., of the glucose monitoring application 116, the computing device 106, and/or server devices of the glucose monitoring platform), crash rate, a number of posts per day (e.g., of the glucose measurements 114 and the event records 122 from the computing device 106 to the glucose monitoring platform 110), packet capture (e.g., of glucose measurements 114 communicated from the wearable glucose monitoring device 104 to the computing device 106)—which may be in terms of a number of packets captured over some period of time (e.g., a day) on a per user basis, a number of data posts (e.g., of glucose measurements 114 and event records 122) per time period (e.g., per day) across the user population 108 to the glucose monitoring platform 110, a number of users of the user population 108 having language code errors, a number or percent of users viewing a glucose trend screen of the glucose monitoring application 116 over a time period (e.g., per day), and so forth.

In one or more implementations, the anomalous behavior 308 indicates which data of the second set of data is anomalous, e.g., which of the second missing events 316 is the anomalous behavior 308. By way of example, the anomalous behavior 308 may indicate which days corresponding to the second missing events 316 have anomalous missing events, e.g., that are above or below the anomaly detection model 306's predicted range. Responsive to output of the anomalous behavior 308 by the anomaly detection model 306, the anomaly detection system 126 may output the anomalous behavior 308 or notifications of the anomalous behavior to one or more users, e.g., developers associated with the glucose monitoring platform 110. The anomaly detection system 126 may output the anomalous behavior 308 and/or notifications about the anomalous behavior in a variety of ways without departing from the spirit or scope of the described techniques, such as by emailing a user designated to receive emails about the anomalous behavior, causing output of a notification on a mobile device of a user designated to receive notifications about the anomalous behavior, causing display of a visualization of the anomalous behavior via a user interface of the anomaly detection system 126, and so on. In the context of displaying a user interface that visually conveys the anomalous behavior 308, consider the following discussion of FIG. 4.

Figure 4:
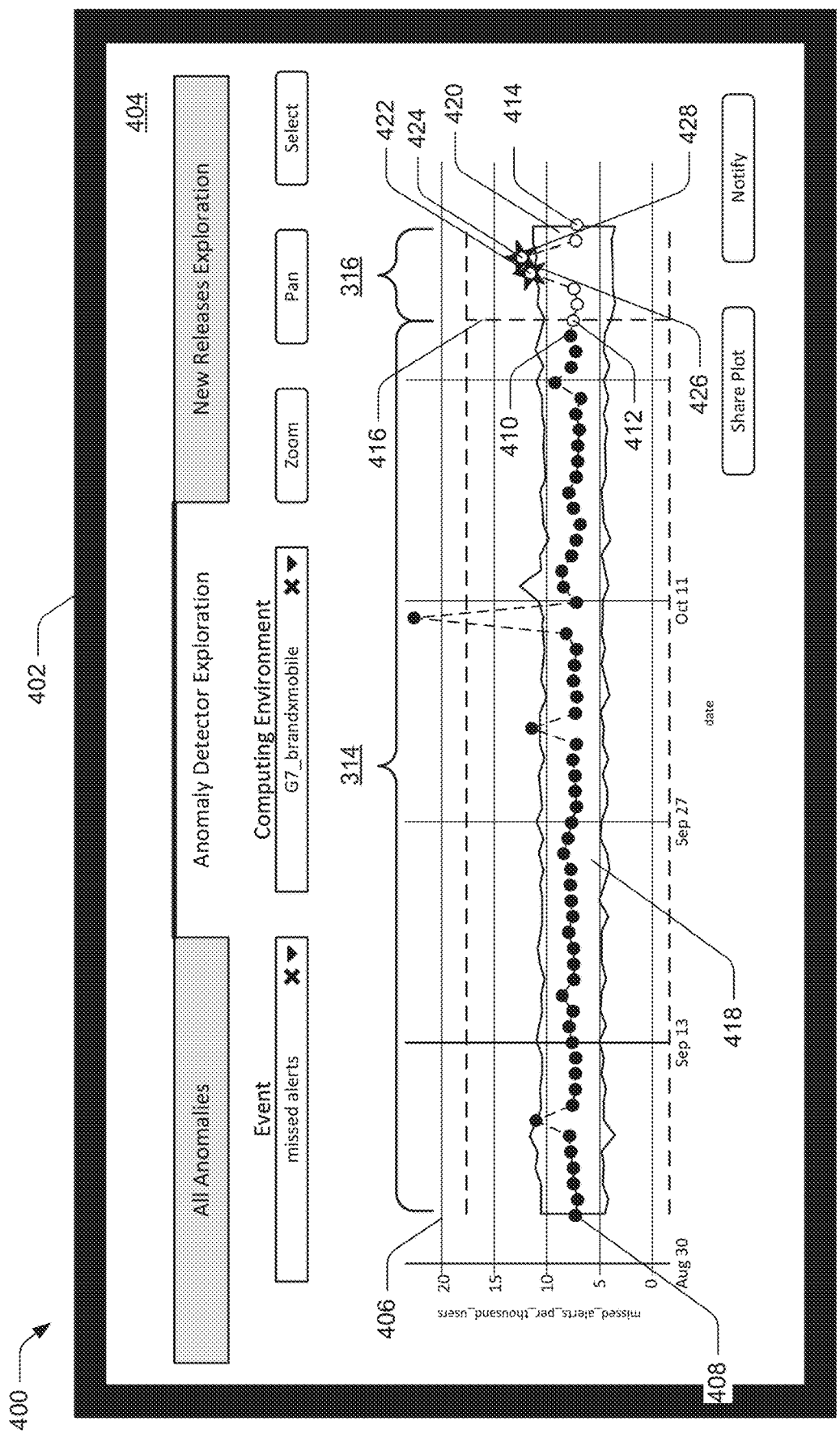
FIG. 4 depicts an example implementation of a user interface displaying a plot of observed behavior associated with a computing environment over time and visualization of a range within which the observed behavior is not anomalous.

FIG. 4 depicts an example 400 of an implementation of a user interface displaying a plot of observed behavior associated with a computing environment over time and visualization of a range within which the observed behavior is not anomalous.

The example 400 includes display device 402 displaying user interface 404, which is associated with the anomaly detection system 126 in accordance with the described techniques, e.g., to visually present anomalies identified within data collected by the glucose monitoring platform 110. Certainly, the anomalous behavior 308 may be presented in other ways in accordance with the described techniques, such as audibly via an audible report.

Here, the user interface 404 includes a graph 406 that plots indications of the first and second missing events 314, 316 over time. In particular, the graph 406 plots a number of missing events per day as indicated by the first and second missing events 314, 316. Event indications 408, 410 are examples of the indications that indicate a number of missing events per day of the first missing events 314, and event indications 412, 414 are examples of the indications that indicate a number of missing events per day of the second missing events 316. The event indications plotted to the left of (e.g., chronologically preceding) anomaly detection time 416 thus correspond to the first missing events 314, and the event indications plotted to the right of (e.g., chronologically subsequent) the anomaly detection time 416 thus correspond to the second missing events 316.

In accordance with the techniques described herein, the anomaly detection model 306 is generated based on data associated with times before the anomaly detection time 416. Additionally, the anomaly detection model 306 is configured to determine anomalies for data associated with times after the anomaly detection time 416. In one or more implementations, the anomaly detection model 306 is configured to determine anomalies for data associated with the anomaly detection time 416, e.g., as depicted in the illustrated example 400. Alternatively, the anomaly detection model may be generated based on data associated with the anomaly detection time 416.

In addition to the plotted event indications, the graph 406 also includes range visualization 418. The range visualization 418 corresponds to the range modeled by the anomaly detection model 306. In this example 400, the range visualization 418 includes a visualization of a predicted range 420, which corresponds to the portion of the range visualization 418 subsequent (e.g., in time) to the anomaly detection time 416. In general, the anomaly detection model 306 uses the predicted range 420 to determine the anomalous behavior 308. In the illustrated example 400, the data that corresponds to the indications outside of the predicted range 420 is anomalous and the data that corresponds to the indications within the predicted range 420 is not anomalous. To this end, indications 422, 424 correspond to the anomalous behavior 308—because they are outside of the predicted range 420. Additionally, those indications 422, 424 are further displayed with visual indicators 426, 428, which indicate that the indications 422, 424 correspond to the anomalous behavior 308. Here, the visual indicators 426, 428 are depicted as stars, however, it is to be appreciated that indications may be emphasized in a variety of ways to indicate that they are anomalous without departing from the spirit or scope of the described techniques. In one or more implementations, the indications that do not include the visual indicators, and for which anomalous behavior is being determined, do not correspond to anomalous behavior.

In this example 400, the user interface 404 includes a variety of instrumentalities that may be user selectable to perform a variety of tasks in relation to the graph 406 and the determined anomalous behavior 308, generally. For example, the user interface 404 may include instrumentalities that enable a user to zoom in or out on the graph 406 (or portions thereof), pan over the graph 406 (or portions thereof or portions not presented), to select various information on the graph (e.g., a displayed indication to cause presentation of further information in relation to a selected indication), to share the graph 406 with one or more other users (e.g., via a link to a web page, via a web-based application, or in a message such as an email), and to notify one or more users about the anomalous behavior (e.g., via email), just to name a few. Certainly, a user interface for presenting the anomalous behavior 308 may be configured to include a variety of instrumentalities that enable different tasks to be performed in relation to the anomalous behavior 308 and its visualization without departing from the spirit or scope of the described techniques.

Figure 5:
FIG. 5 depicts an example implementation of a user interface displaying a notification of detected anomalous behavior.

FIG. 5 depicts an example 500 of an implementation of a user interface displaying a notification of detected anomalous behavior.

In this example 500, computing device 502 is depicted displaying user interface 504 (e.g., a lock screen) via a display device 506 of the computing device 502. Here, notification 508 is further presented via the user interface 504. The notification 508 includes information about detected anomalous behavior, e.g., the anomalous behavior 308. By way of example, the anomaly detection system 126 may cause the notification 508 to be displayed at the computing device 502 for a user associated with the anomaly detection system 126, e.g., a developer associated with the glucose monitoring platform 110 that is designated to receive notifications about one or more types of detected anomalous behavior. Users may be notified in a variety of other ways about the anomalous behavior 308 (e.g., by email) without departing from the spirit or scope of the described techniques.

Having discussed exemplary details of the techniques for detection of anomalous computing environment behavior using glucose, consider now some examples of procedures to illustrate additional aspects of the techniques.

Example Procedures

This section describes examples of procedures for detecting anomalous computing environment behavior using glucose. Aspects of the procedures may be implemented in hardware, firmware, or software, or a combination thereof. The procedures are shown as a set of blocks that specify operations performed by one or more devices and are not necessarily limited to the orders shown for performing the operations by the respective blocks. In at least some implementations the procedures are performed by an anomaly detection system, such as the anomaly detection system 126 that makes use of the event engine simulator 130, the compare model 302, the model manager 304, and the anomaly detection model 306.

Figure 6:
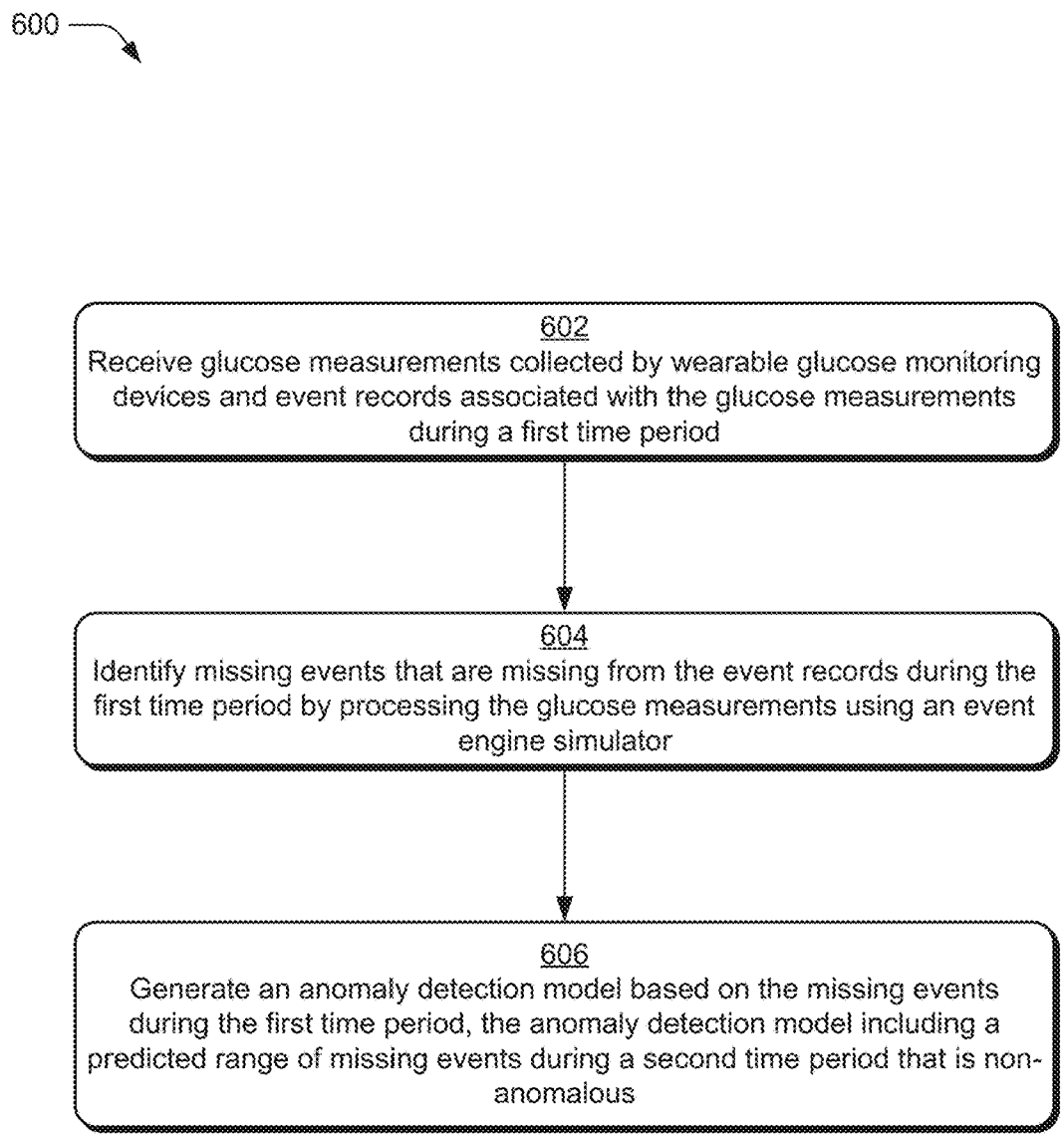
FIG. 6 depicts a procedure in an example implementation in which an anomaly detection model is generated based on missing events identified during a first time period.

FIG. 6 depicts a procedure 600 in an example of an implementation in which an anomaly detection model is generated based on missing events identified during a first time period.

Glucose measurements collected by wearable glucose monitoring devices and event records associated with the glucose measurements are received during a first time period (block 602). By way of example, the anomaly detection system 126 receives glucose measurements 114 collected by wearable glucose monitoring devices 104 and event records 122 as input during a first time period.

Missing events that are missing from the event records are identified during the first time period by processing the glucose measurements using an event engine simulator (block 604). By way of example, an event engine simulator 130 of the anomaly detection system 126 processes the glucose measurements 114 obtained during the first time period to generate simulated events 310. A compare module 302 of the anomaly detection system 126 then compares the simulated events 310 to recorded events in the event records 122 that were actually generated by an event engine of glucose monitoring applications associated with the respective wearable glucose monitoring devices 104. By way of example and not limitation, the compare module 302 may extract a first event from the simulated events 310 and iterate over the actual events stored in the event records 122 to determine whether an actual event corresponding to the first event is included in the event records 122. If an actual event that corresponds to the first event is included in the event records 122, then the compare module 302 may proceed by extracting a second event from the simulated events 310 and iterating over the events in the event records 122 to determine whether an actual event corresponding to the second event is included in the event records.

However, if an actual event that corresponds to the first event is not included in the event records 122, then the compare module 302 may determine that the first event corresponds to a first missing event 314 from the event records 122. The compare module 302 may output the first missing events 314 or otherwise maintain a record of first missing events 314, such as a counter that increments each time a missing event is determined, references (e.g., a list of identifiers) to each of the simulated events 310 that is determined to be missing from the event records 122, and/or a list of the determined missing events (e.g., which include details of the event similar to how an event is recorded by the event engine 120), to name just a few. The compare module 302 may process each of the simulated events 310 in a similar fashion to determine whether they are included in the event records or not.

An anomaly detection model is generated based on the missing events during the first time period (block 606). In accordance with the principles discussed herein, the anomaly detection model includes a predicted range of missing events during a second time period. By way of example, the model manager 304 of the anomaly detection system 126 is configured to generate or otherwise train the anomaly detection model 306. The model manager 304 may generate the anomaly detection model 306 according to a variety of algorithms. In particular, the model manager 304 may generate or otherwise train the anomaly detection model based on a first set of time-ordered historical data, e.g., the first missing events 314. Once the model manager 304 generates the anomaly detection model 306, the anomaly detection model 306 is configured to determine whether there are anomalies in a second set of time-ordered data, e.g., whether there are anomalies in the second missing events 316.

Figure 7:
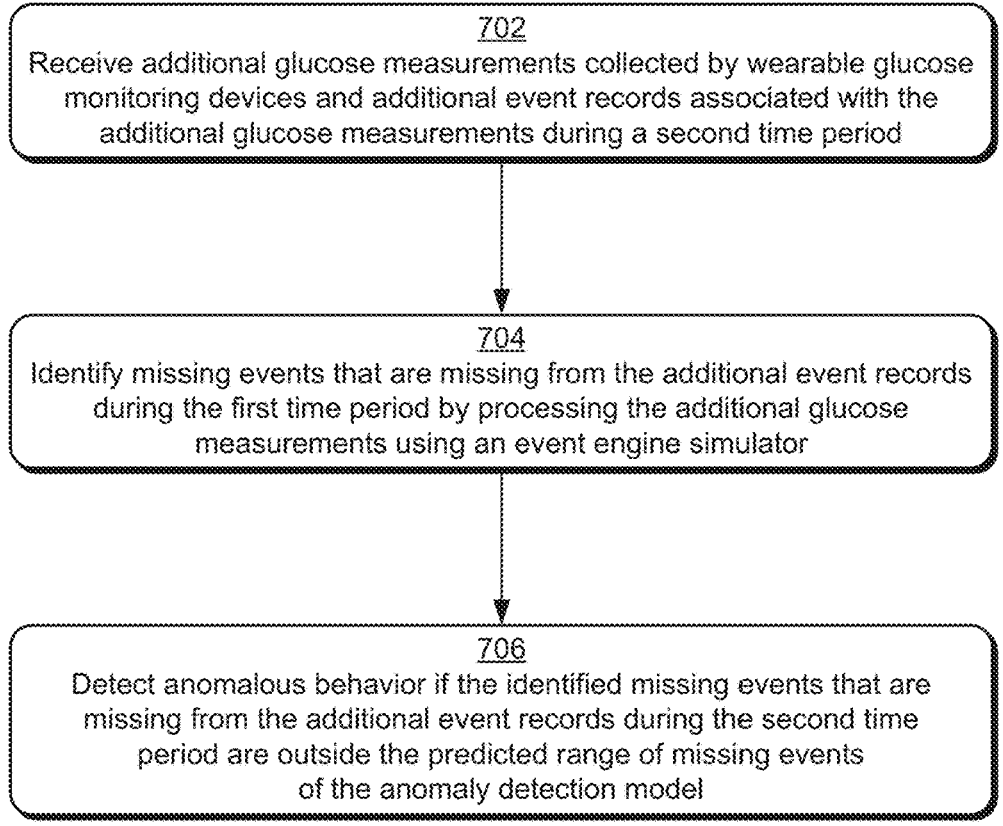
FIG. 7 depicts a procedure in an example implementation in which the anomaly detection model generated in FIG. 6 is utilized to detect anomalous behavior during a second time period.

In the context of using the anomaly detection model to determine whether there are anomalies in a second set of time-ordered data, consider FIG. 7 which depicts a procedure 700 in an example of an implementation in which the anomaly detection model generated in FIG. 6 is utilized to detect anomalous behavior during a second time period.

Additional glucose measurements collected by the wearable glucose monitoring devices and additional event records associated with the additional glucose measurements are received during the second time period (block 702). By way of example, the anomaly detection system 126 receives glucose measurements 114 collected by wearable glucose monitoring devices 104 and event records 122 as input during a second time period. Notably, the first time period may precede the second time period.

Missing events that are missing from the additional event records are identified during the second time period by processing the additional glucose measurements using the event engine simulator (block 704). By way of example, and similar to block 604 of FIG. 6, the event engine simulator 130 of the anomaly detection system 126 processes the glucose measurements 114 obtained during the second time period to generate simulated events 310. A compare module 302 of the anomaly detection system 126 then compares the simulated events 310 to recorded events in the event records 122 that were actually generated by an event engine of glucose monitoring applications associated with the respective wearable glucose monitoring devices 104 during the second time period. If an actual event that corresponds to a simulated event 310 is not included in the event records 122, then the compare module 302 may determine that the simulated event corresponds to a second missing event 316 from the event records 122. The compare module 302 may output the second missing events 316 or otherwise maintain a record of second missing events 316. Notably, the first missing events 314 may correspond to times that precede a point in time and the second missing events 316 may correspond to the point in time and/or times that are subsequent to the point in time. Given the example where the anomaly detection model 306 determines the anomalous behavior 308 for a preceding week based on eight weeks of events before that week, the first missing events 314 may correspond to weeks 2-9 and the second missing events 316 may correspond to week 1, where week 9 is the furthest week in the past from a current time and week 1 is the nearest week in the past from the current time.

Anomalous behavior is detected if the identified missing events that are missing from the additional event records during the second time period are outside the predicted range of missing events of the anomaly detection model (block 706). By way of example, the anomaly detection model 306 outputs the anomalous behavior 308 responsive to processing the data that the models determines is outside the predicted range. In the context of missing events, the missing events described by the second missing events 316 (e.g., a number or percent of missing events per day) that fall within the anomaly detection model 306's predicted range (e.g., configured also as a number or percent of missing events per day) are not anomalous. However, the missing events described by the second missing events 316 (e.g., a number or percent of missing events per day) that fall outside the anomaly detection model 306's predicted range (e.g., configured also as a number or percent of missing events per day) are anomalous. For these anomalous events, the anomaly detection model 306 outputs the anomalous behavior 308.

Having described examples of procedures in accordance with one or more implementations, consider now an example of a system and device that can be utilized to implement the various techniques described herein.

Example System and Device

Figure 8:
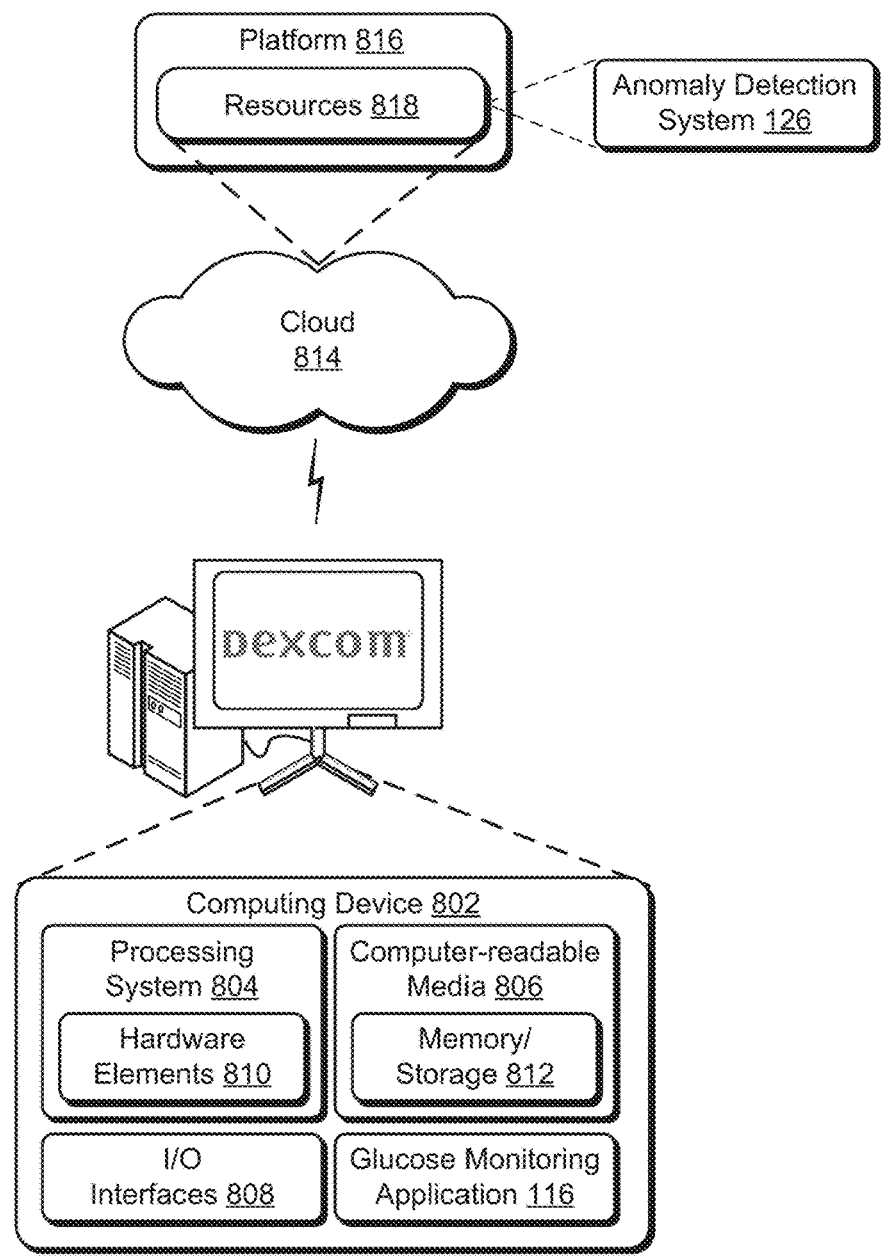
FIG. 8 illustrates an example of a system including various components of an example device that can be implemented as any type of computing device as described and/or utilized with reference to FIGS. 1-7 to implement embodiments of the techniques described herein.

FIG. 8 illustrates an example of a system generally at 800 that includes an example of a computing device 802 that is representative of one or more computing systems and/or devices that may implement the various techniques described herein. This is illustrated through inclusion of the anomaly detection system 126 and the glucose monitoring platform 110. The computing device 802 may be, for example, a server of a service provider, a device associated with a client (e.g., a client device), an on-chip system, and/or any other suitable computing device or computing system.

The example computing device 802 as illustrated includes a processing system 804, one or more computer-readable media 806, and one or more I/O interfaces 808 that are communicatively coupled, one to another. Although not shown, the computing device 802 may further include a system bus or other data and command transfer system that couples the various components, one to another. A system bus can include any one or combination of different bus structures, such as a memory bus or memory controller, a peripheral bus, a universal serial bus, and/or a processor or local bus that utilizes any of a variety of bus architectures. A variety of other examples are also contemplated, such as control and data lines.

The processing system 804 is representative of functionality to perform one or more operations using hardware. Accordingly, the processing system 804 is illustrated as including hardware elements 810 that may be configured as processors, functional blocks, and so forth. This may include implementation in hardware as an application specific integrated circuit or other logic device formed using one or more semiconductors. The hardware elements 810 are not limited by the materials from which they are formed or the processing mechanisms employed therein. For example, processors may be comprised of semiconductor(s) and/or transistors (e.g., electronic integrated circuits (ICs)). In such a context, processor-executable instructions may be electronically-executable instructions.

The computer-readable media 806 is illustrated as including memory/storage 812. The memory/storage 812 represents memory/storage capacity associated with one or more computer-readable media. The memory/storage component 812 may include volatile media (such as random access memory (RAM)) and/or nonvolatile media (such as read only memory (ROM), Flash memory, optical disks, magnetic disks, and so forth). The memory/storage component 812 may include fixed media (e.g., RAM, ROM, a fixed hard drive, and so on) as well as removable media (e.g., Flash memory, a removable hard drive, an optical disc, and so forth). The computer-readable media 806 may be configured in a variety of other ways as further described below.

Input/output interface(s) 808 are representative of functionality to allow a user to enter commands and information to computing device 802, and also allow information to be presented to the user and/or other components or devices using various input/output devices. Examples of input devices include a keyboard, a cursor control device (e.g., a mouse), a microphone, a scanner, touch functionality (e.g., capacitive or other sensors that are configured to detect physical touch), a camera (e.g., which may employ visible or non-visible wavelengths such as infrared frequencies to recognize movement as gestures that do not involve touch), and so forth. Examples of output devices include a display device (e.g., a monitor or projector), speakers, a printer, a network card, tactile-response device, and so forth. Thus, the computing device 802 may be configured in a variety of ways as further described below to support user interaction.

Various techniques may be described herein in the general context of software, hardware elements, or program modules. Generally, such modules include routines, programs, objects, elements, components, data structures, and so forth that perform particular tasks or implement particular abstract data types. The terms "module," "functionality," and "component" as used herein generally represent software, firmware, hardware, or a combination thereof. The features of the techniques described herein are platform-independent, meaning that the techniques may be implemented on a variety of commercial computing platforms having a variety of processors.

An implementation of the described modules and techniques may be stored on or transmitted across some form of computer-readable media. The computer-readable media may include a variety of media that may be accessed by the computing device 802. By way of example, and not limitation, computer-readable media may include "computer-readable storage media" and "computer-readable signal media."

"Computer-readable storage media" may refer to media and/or devices that enable persistent and/or non-transitory storage of information in contrast to mere signal transmission, carrier waves, or signals per se. Thus, computer-readable storage media refers to non-signal bearing media. The computer-readable storage media includes hardware such as volatile and non-volatile, removable and non-removable media and/or storage devices implemented in a method or technology suitable for storage of information such as computer readable instructions, data structures, program modules, logic elements/circuits, or other data. Examples of computer-readable storage media may include, but are not limited to, RAM, ROM, EEPROM, flash memory or other memory technology, CD-ROM, digital versatile disks (DVD) or other optical storage, hard disks, magnetic cassettes, magnetic tape, magnetic disk storage or other magnetic storage devices, or other storage device, tangible media, or article of manufacture suitable to store the desired information and which may be accessed by a computer.

"Computer-readable signal media" may refer to a signal-bearing medium that is configured to transmit instructions to the hardware of the computing device 802, such as via a network. Signal media typically may embody computer readable instructions, data structures, program modules, or other data in a modulated data signal, such as carrier waves, data signals, or other transport mechanism. Signal media also include any information delivery media. The term "modulated data signal" means a signal that has one or more of its characteristics set or changed in such a manner as to encode information in the signal. By way of example, and not limitation, communication media include wired media such as a wired network or direct-wired connection, and wireless media such as acoustic, RF, infrared, and other wireless media.

As previously described, hardware elements 810 and computer-readable media 806 are representative of modules, programmable device logic and/or fixed device logic implemented in a hardware form that may be employed in some embodiments to implement at least some aspects of the techniques described herein, such as to perform one or more instructions. Hardware may include components of an integrated circuit or on-chip system, an application-specific integrated circuit (ASIC), a field-programmable gate array (FPGA), a complex programmable logic device (CPLD), and other implementations in silicon or other hardware. In this context, hardware may operate as a processing device that performs program tasks defined by instructions and/or logic embodied by the hardware as well as a hardware utilized to store instructions for execution, e.g., the computer-readable storage media described previously.

Combinations of the foregoing may also be employed to implement various techniques described herein. Accordingly, software, hardware, or executable modules may be implemented as one or more instructions and/or logic embodied on some form of computer-readable storage media and/or by one or more hardware elements 810. The computing device 802 may be configured to implement particular instructions and/or functions corresponding to the software and/or hardware modules. Accordingly, implementation of a module that is executable by the computing device 802 as software may be achieved at least partially in hardware, e.g., through use of computer-readable storage media and/or hardware elements 810 of the processing system 804. The instructions and/or functions may be executable/operable by one or more articles of manufacture (for example, one or more computing devices 802 and/or processing systems 804) to implement techniques, modules, and examples described herein.

The techniques described herein may be supported by various configurations of the computing device 802 and are not limited to the specific examples of the techniques described herein. This functionality may also be implemented all or in part through use of a distributed system, such as over a "cloud" 814 via a platform 816 as described below.

The cloud 814 includes and/or is representative of a platform 816 for resources 818. The platform 816 abstracts underlying functionality of hardware (e.g., servers) and software resources of the cloud 814. The resources 818 may include applications and/or data that can be utilized while computer processing is executed on servers that are remote from the computing device 802. Resources 818 can also include services provided over the Internet and/or through a subscriber network, such as a cellular or Wi-Fi network.

The platform 816 may abstract resources and functions to connect the computing device 802 with other computing devices. The platform 816 may also serve to abstract scaling of resources to provide a corresponding level of scale to encountered demand for the resources 818 that are implemented via the platform 816. Accordingly, in an interconnected device embodiment, implementation of functionality described herein may be distributed throughout the system 800. For example, the functionality may be implemented in part on the computing device 802 as well as via the platform 816 that abstracts the functionality of the cloud 814.

CONCLUSION

Although the systems and techniques have been described in language specific to structural features and/or methodological acts, it is to be understood that the systems and techniques defined in the appended claims are not necessarily limited to the specific features or acts described. Rather, the specific features and acts are disclosed as example forms of implementing the claimed subject matter.

What is claimed is:

1. A method executed by one or more processors, the method comprising:
   receiving glucose measurements collected by wearable glucose monitoring devices and event records associated with the glucose measurements during a first time period and a second time period;
   identifying missing events that are missing from the event records during the first time period and the second time period by processing the glucose measurements using an event engine simulator;
   training an anomaly detection machine learning model based on the identified missing events during the first time period;
   predicting, using the anomaly detection machine learning model, a non-anomalous range of missing events for the second time period;
   determining anomalous behavior for the second time period based on the identified missing events during the second time period and the predicted non-anomalous range of missing events for the second time period; and
   outputting the anomalous behavior.

2. The method of claim 1, wherein identifying the missing events that are missing from the event records during the first time period and the second time period further comprises:
   processing the glucose measurements using the event engine simulator to generate simulated events; and
   comparing the simulated events to actual events in the event records during the first time period and the second time period to identify the missing events that are missing from the event records during the first time period and the second time period.

3. The method of claim 2, wherein the missing events comprise the simulated events which do not have a matching actual event in the event records during the first time period and the second time period.

4. The method of claim 1, wherein the event engine simulator comprises a replication of an event engine of a glucose monitoring application associated with the wearable glucose monitoring devices.

5. The method of claim 1, wherein the predicted non-anomalous range of missing for the second time period corresponds to a predicted range of missing events per day that is non-anomalous, and wherein detecting the anomalous behavior comprises detecting the anomalous behavior when the missing events during the second time period for a first day during the second time period are outside the predicted range of missing events per day that is non-anomalous.

6. The method of claim 5, further comprising detecting non-anomalous behavior when the missing events during the second time period for a second day during the second time period are within the predicted range of missing events per day that is non-anomalous.

7. The method of claim 1, wherein the event records include low glucose alerts generated by the wearable glucose monitoring devices during the first time period.

8. The method of claim 1, wherein the first time period precedes the second time period.

9. The method of claim 1, further comprising causing display of an anomalous behavior user interface that plots the missing events during the first time period and the second time period.

10. The method of claim 9, wherein the anomalous behavior user interface visually indicates the predicted non-anomalous range of missing events.

11. The method of claim 10, wherein the missing events that are plotted outside the predicted non-anomalous range of missing events are displayed with a visual indicator to indicate that the missing events correspond to the anomalous behavior.

12. A computer-readable storage device comprising stored instructions that, responsive to execution by one or more processors, cause the one or more processor to perform operations comprising:
   receiving glucose measurements collected by wearable glucose monitoring devices and event records associated with the glucose measurements during a first time period and a second time period;
   identifying missing events that are missing from the event records during the first time period and the second time period by processing the glucose measurements using an event engine simulator;

training an anomaly detection machine learning model based on the identified missing events during the first time period;

predicting, using the anomaly detection machine learning model, a non-anomalous range of missing events for the second time period;

determining anomalous behavior for the second time period based on the identified missing events during the second time period and the predicted non-anomalous range of missing events for the second time period; and outputting the anomalous behavior.

13. The computer-readable storage device of claim 12, wherein identifying the missing events that are missing from the event records during the first time period and the second time period further comprises:

processing the glucose measurements using the event engine simulator to generate simulated events; and comparing the simulated events to actual events in the event records during the first time period and the second time period to identify the missing events that are missing from the event records during the first time period and the second time period.

14. The computer-readable storage device of claim 13, wherein the missing events comprise the simulated events which do not have a matching actual event in the event records during the first time period and the second time period.

15. The computer-readable storage device of claim 12, wherein the event engine simulator comprises a replication of an event engine of a glucose monitoring application associated with the wearable glucose monitoring devices.

16. The computer-readable storage device of claim 12, wherein the predicted non-anomalous range of missing events for the second time period corresponds to a predicted range of missing events per day that is non-anomalous, and wherein detecting the anomalous behavior comprises detecting the anomalous behavior when the missing events during the second time period for a first day during the second time period are outside the predicted range of missing events per day that is non-anomalous.

17. The computer-readable storage device of claim 16, wherein the operations further comprise detecting non-anomalous behavior when the missing events during the second time period for a second day during the second time period are within the predicted range of missing events per day that is non-anomalous.

18. The computer-readable storage device of claim 12, wherein the event records include low glucose alerts generated by the wearable glucose monitoring devices during the first time period.

19. The computer-readable storage device of claim 12, wherein the first time period precedes the second time period.

20. The computer-readable storage device of claim 12, wherein the operations further comprise causing display of an anomalous behavior user interface that plots the missing events during the first time period and the second time period.

21. The computer-readable storage device of claim 20, wherein the anomalous behavior user interface visually indicates the predicted non-anomalous range of missing events.

22. The computer-readable storage device of claim 21, wherein the missing events that are plotted outside the predicted non-anomalous range of missing events are displayed with a visual indicator to indicate that the missing events correspond to the anomalous behavior.

23. A computing system comprising:

one or more memories comprising executable instructions;

one or more processors in data communication with the one or more memories and configured to execute the executable instructions to:

receive glucose measurements collected by wearable glucose monitoring devices and event records associated with the glucose measurements during a first time period and a second time period;

identify missing events that are missing from the event records during the first time period and the second time period by processing the glucose measurements using an event engine simulator;

train an anomaly detection machine learning model based on the identified missing events during the first time period;

predict, using the anomaly detection machine learning model, a non-anomalous range of missing events for the second time period;

determine anomalous behavior for the second time period based on the identified missing events during the second time period and the predicted non-anomalous range of missing events for the second time period; and output the anomalous behavior.

* * * * *